United States Patent
Weinacht et al.

(10) Patent No.: US 7,892,225 B2
(45) Date of Patent: Feb. 22, 2011

(54) DEVICES AND METHODS FOR SEPARATING LAYERS OF MATERIALS HAVING DIFFERENT ABLATION THRESHOLDS

(75) Inventors: Martin Weinacht, Herxheim (DE); Frieder Loesel, Mannheim (DE); Tobias Kuhn, Jena (DE)

(73) Assignee: Technolas Perfect Vision GmbH, Munich (DE)

( * ) Notice: Subject to any disclaimer, the term of this patent is extended or adjusted under 35 U.S.C. 154(b) by 1791 days.

(21) Appl. No.: 11/015,338

(22) Filed: Dec. 17, 2004

(65) Prior Publication Data

US 2007/0078447 A1   Apr. 5, 2007

(51) Int. Cl.
*A61B 18/18* (2006.01)
(52) U.S. Cl. .................... 606/5; 606/4; 606/12; 607/89
(58) Field of Classification Search ........................ None
See application file for complete search history.

(56) References Cited

U.S. PATENT DOCUMENTS

| | | | |
|---|---|---|---|
| 4,884,884 A | 12/1989 | Reis | |
| 4,887,019 A | 12/1989 | Reis et al. | |
| 4,887,592 A | 12/1989 | Loertscher | |
| 4,907,586 A | 3/1990 | Bille et al. | |
| 4,988,348 A | 1/1991 | Bille | |
| 4,994,058 A | 2/1991 | Raven et al. | |
| 5,480,396 A | 1/1996 | Simon et al. | |
| 5,984,916 A | 11/1999 | Lai | |
| 5,993,438 A | 11/1999 | Juhasz et al. | |
| 6,110,166 A | 8/2000 | Juhasz | |
| 6,331,177 B1 | 12/2001 | Munnerlyn et al. | |
| 6,451,006 B1 | 9/2002 | Bille | |
| 2002/0111607 A1* | 8/2002 | Bille | 606/5 |
| 2003/0212387 A1 | 11/2003 | Kurtz et al. | |
| 2006/0106371 A1* | 5/2006 | Muhlhoff et al. | 606/5 |

FOREIGN PATENT DOCUMENTS

| | | |
|---|---|---|
| EP | 1316298 A2 | 6/2003 |
| EP | 1473006 A1 | 11/2004 |

* cited by examiner

*Primary Examiner*—Henry M Johnson, III
*Assistant Examiner*—Lynsey Crandall
(74) *Attorney, Agent, or Firm*—Nydegger & Associates

(57) ABSTRACT

A method and device for photoablation is disclosed wherein photoablation occurs along the interface between a material having a lower energy ablation threshold and a material having a higher energy ablation threshold. The method and device utilize a laser beam having a beam energy density which is less than the higher energy ablation threshold and greater than or equal to the lower energy ablation threshold. By directing such a laser beam to the interface, the material having the lower energy threshold is photoablated while the material having the higher energy threshold is largely unaffected.

15 Claims, 4 Drawing Sheets

DEVICES AND METHODS FOR SEPARATING LAYERS OF MATERIALS HAVING DIFFERENT ABLATION THRESHOLDS

FIELD OF THE INVENTION

The present invention pertains generally to laser surgery procedures. More particularly, the present invention relates to methods and devices for performing intra-material photoablation wherein the energy density of the focused laser beam is selected in accordance with characteristics of the material to be ablated. The present invention is particularly, but not exclusively, useful as a method and device for precise photoablation at the interface between materials that have different laser induced optical breakdown thresholds.

BACKGROUND OF THE INVENTION

In the last few years, ultra short pulsed laser systems have become widely available for commercial applications. One application of such ultra short pulsed lasers involves intra-material ablation. For intra-material ablation, the local electrical field strength at the focal point of the laser (usually measured in $J/cm^2$ or equivalent units) must be equal to or greater than the binding energy of the material's valence electrons to their atoms. When the beam's energy density is equal to or greater than the material's energy density threshold, a laser induced optical breakdown (LIOB) of the material occurs at or near the focal point. During LIOB, a microplasma, gas bubbles and shockwaves are generated.

With the above in mind, consideration is given here for the use of an ultra short pulsed laser for photoablating a selected material without affecting the adjacent non-selected material. Specifically, consideration is given for the use of such photoablation where adjacent materials have different ablation thresholds.

In considering details of a photoablation procedure, the geometry and intensity distribution of a laser beam should be understood. In particular, the shape of the laser focus can be assumed to be hyperbolic, and the intensity distribution can be assumed to be Gaussian. With these assumptions, the laser focus has a minimum radius (the beam waist) and has a length (or focal depth). The boundary of the laser beam is usually defined by the position where the intensity of the beam has decreased to $1/e^2$ of the intensity in the center of the beam.

With a known ablation threshold for LIOB, it might be expected that the location where LIOB occurs within the laser focus can be simply determined by the position where the necessary energy density is reached. Therefore, the position of LIOB within a material could be changed not only by moving the position of the laser focus, but also by altering the beam energy. In other words, the intensity needed for LIOB scales with the size of the laser focus. However, this relationship is based on the assumption that the whole energy of the laser pulse is instantaneously deposited within the material. In reality, the intensity (and, thus, the energy) of the laser beam also has a distribution along the z-axis that is determined by the pulse length and shape of the laser pulse and can be described by a $sech^2$-curve. This leads to a spatial distribution of the intensity along the z-axis. As a consequence, LIOB occurs only when the intensity of the laser pulse reaches the threshold intensity needed for LIOB.

If the threshold for LIOB changes along the z-axis (e.g., at the interface between two materials), then the position of LIOB changes significantly. For instance, a laser may induce LIOB at its focal point in one material but have no effect when another material is used. Therefore, appropriate settings for beam geometry and beam energy can be used to control the position of LIOB at the interface of two materials having different ablation thresholds. If the ablation thresholds for the materials are known, or can be identified, the energy level can be calculated to provide LIOB in only one of the materials. Furthermore, by identifying the position of the interface before activating the laser, the focal point may be initially positioned in the targeted material with the appropriate energy level to avoid any unintentional ablation. After the laser beam has been activated, detecting means may be used to detect whether LIOB has occurred and, if so, in which material. Such detection may be through analysis of the size of the bubble resulting from LIOB or through spectral analysis of the plasma resulting from LIOB.

While intra-material photoablation may be performed on various materials, its use on corneal tissue or biological tissue is of particular interest. With regard to corneal tissue, it is noted that several surgical procedures exist for modifying its structure. To understand these procedures, the operation and anatomy of the cornea should be understood.

Along with the lens, the cornea refracts incoming light and focuses the light on or near the retina. The curvature of the cornea determines where the incoming light will be focused. If the curvature of the cornea is too steep or too flat, it may be modified by photoablating certain corneal tissue. Anatomically, the structurally distinct corneal tissues include, in order from the anterior to the posterior of the eye, the epithelium, Bowman's membrane, the stroma, Descemet's membrane, and the endothelium. Of these, the stroma is the most extensive, being generally around four hundred microns thick. Consequently, the stroma provides the most opportunity for correction via photoablation. Additionally, the healing response of the stroma is typically quicker than the other corneal layers.

In the past, techniques such as laser-assisted in situ keratomileusis (LASIK) and laser epithelial keratomileusis (LASEK) have been used to reshape stromal tissue. In these procedures, stromal tissue is ablated after being exposed by temporarily removing the overlying tissues. Other ophthalmic procedures rely on subsurface photoablation, i.e., the photoablation of stromal tissue without first exposing the tissue through the removal of overlying tissue. Because the subsurface photoablative procedures provide clear benefits over the prior art's reliance on the removal of overlying tissues, further efforts have been made to utilize intracorneal photoablative techniques. Specifically, these efforts have involved the use of ultra short pulsed laser systems in intracorneal photoablation procedures. As a result of these efforts, an intracorneal technique has been discovered that allows precise separation of corneal tissues along their interface using an ultra short (femto-second) pulsed laser.

In light of the above, it is an object of the present invention to provide an efficient surgical method for creating a discontinuity at the interface between two distinct materials. Another object of the present invention is to provide a method and device for separating two distinct materials having different ablation energy thresholds. It is yet another object of the present invention to provide a surgical method and device for creating a corneal flap that allows for the accurate positioning of the corneal flap at a predetermined location on the cornea. Still another object of the present invention is to provide a method for intra-material photoablation along an interface that is easy to perform and is comparatively cost effective.

SUMMARY OF THE INVENTION

A device for performing photoablation along an interface between materials includes a source for creating a laser beam having a energy density less than the non-targeted material's energy ablation threshold and greater than or equal to the targeted material's energy ablation threshold. The device further includes a means for directing the laser beam to the interface to photoablate a portion of the targeted material adjacent the interface. A means for scanning the laser beam along the interface provides for photoablation of further portions of targeted material adjacent the interface.

In use, the energy ablation thresholds of the two materials are identified. Specifically, the materials, which may be corneal or biological tissues, must be identified as having different energy thresholds for ablation. After the ablation thresholds are identified, an ultra short pulsed laser beam is created by selecting a beam geometry, beam energy and pulse duration. These selections are made to create a laser beam having a desired maximum beam energy density. This desired maximum energy density is less than the ablation threshold of the non-targeted material but greater than or equal to the ablation threshold of the targeted material. After selection of the beam parameters, the beam is employed to photoablate the targeted material adjacent the interface. Despite the use of the laser beam at the interface, the non-targeted material is unharmed.

In accordance with the present invention, the interface can be found by employing means such as a confocal microscope or an optical coherence tomograph. After finding the interface, the laser beam may be directed thereto to photoablate the targeted material. Specifically, the laser beam is focused to a focal point where the beam reaches its maximum beam energy density. Additionally, the focused beam has a minimum beam energy density that is defined herein to be equal to the threshold of the targeted material. The minimum beam energy is created either at, or spaced from, the focal point. When directing the beam to the interface, the focal point is preferably located in the non-targeted material. In this way, the method avoids or minimizes inadvertent photoablation of targeted material when the laser beam is generated.

Preferably, the focal point is located in the non-targeted portion by setting the appropriate distance between the focal point and the laser source. However, the focal point may be located in the non-targeted portion by more generally situating the focal point in the cornea and then generating the laser beam. After the beam is generated, a sensing means is used to sense whether any targeted material is photoablated. If no targeted material is photoablated, then the focal point can be identified as being in the non-targeted material. If targeted material is photoablated, then the focal point is resituated away from the non-interface boundary of the targeted material. Then the beam is generated and the sensing means is used to determine if any targeted material is photoablated. These steps may be repeated until the focal point is identified as being in the non-targeted material.

After the focal point is located in the non-targeted material and the laser beam is generated, the response of the targeted material is detected. For instance, a photoablative result can be confirmed by the size of the bubble, or the spectral analysis of the plasma, created by photoablation. If no targeted material is photoablated, then either the focal point is moved toward the targeted material, or the beam energy is increased (though not to the threshold of the non-targeted material). It is noted that either of these steps will effectively advance the minimum beam energy density toward the interface. After one of, or a combination of, the steps is taken, the laser beam is again generated and the detecting means detects whether any targeted material has been photoablated. If not, the minimum beam energy density is again advanced toward the interface. Preferably, these steps are repeated until the portion of targeted material adjacent the interface and nearest the focal point is photoablated.

Once photoablation of the targeted material adjacent the interface is detected, the laser beam is scanned to another location. Then the previous steps are repeated to photoablate a further portion of the targeted material. Preferably, the laser beam is utilized in this manner to form a periphery for a flap. Such a flap is formed by incising the cornea between the anterior surface of the cornea and the periphery. The targeted and non-targeted materials can then be separated along the periphery by mechanically peeling the non-targeted material and the targeted material from one another.

While certain embodiments are described above, other alternate embodiments are contemplated by the present invention. For instance, the method may be used to photoablate non-corneal tissue and non-biological tissue. In addition, a wavefront detector or other means may be utilized rather than, or in addition to, a confocal microscope or an optical coherence tomography.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENTS

Figure 1:
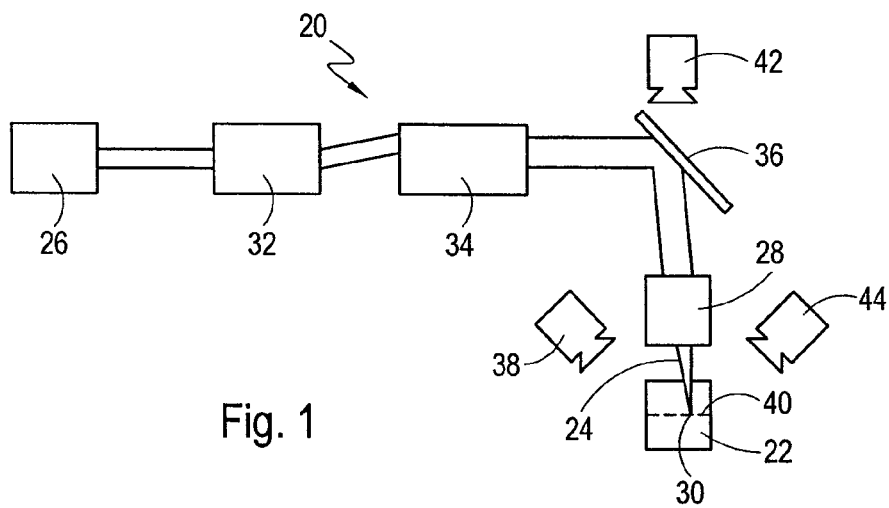
FIG. 1 is a plan view of an embodiment of the ultra short pulsed laser system of the present invention.

Referring initially to FIG. 1, a laser system 20 is shown for conducting a intracorneal laser procedure on an eye 22. As shown, the eye 22 is aligned to receive an ultra short pulsed laser beam 24 from the laser system 20. As detailed further below, the pulsed laser beam 24 having selected parameters is generated by a laser source 26. The laser system 20 includes a focusing unit 28 for focusing the beam 24 to its focal point 30. Also included in the laser system 20 is a scanning unit 32 for directing the beam 24. In addition to the laser source 26 and focusing unit 28, the laser system 20 includes a scanning unit 32 for directing the laser beam 24. Also provided in the system 20 is a telescope 34 for collimating the beam 24 after it is directed by the scanner 32. Downstream of the telescope 34 is a reflector 36 that redirects the laser beam 24 toward the eye 22 through the focusing unit 28.

While not directly involved with the generation and control of the laser beam 24, several sensors are also provided in the laser system 20. Specifically, the system 20 includes a sensor 38, preferably a confocal microscope or an optical coherence tomograph, for finding the interface 40 at which photoablation is desired. The system 20 further includes a sensor 42 for detecting whether and where photoablation has occurred. The system 20 may include an additional sensor or sensors 44 for identifying photoablation thresholds as discussed below.

In accordance with the present invention, photoablation can be performed to provide intracorneal tissue modification to effect a refractive change in the cornea, to create a flap suitable for a LASIK or LASEK type procedure, to create a passageway or drainage channel in the eye 22, or to effect any other type of surgical procedure, in whole or in part, known in the pertinent art that requires the removal of ocular tissue.

Figure 2:
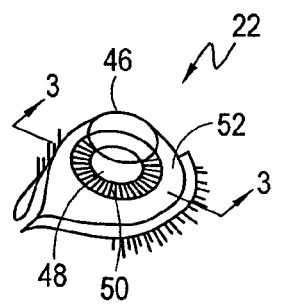
FIG. 2 is perspective view of an eye.
Figure 3:
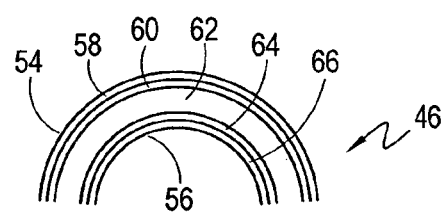
FIG. 3 is a cross sectional view, not to scale, of a portion of the cornea of the eye as seen along line 3-3 in FIG. 2 showing the anatomical layers of the cornea.

FIG. 2 shows the anatomical structure of the human eye 22 including the cornea 46, the pupil 48, the iris 50, and the sclera 52. In FIG. 3 it can be seen that the cornea 46 includes five anatomically definable layers of tissue. Going in a direction from anterior 54 to posterior 56 in FIG. 3, the tissue layers of the cornea 46 are: the epithelium 58, Bowman's membrane 60, the stroma 62, Descemet's membrane 64 and the endothelium 66. These corneal layers have distinct photoablation thresholds. For instance, depending on the laser pulse length, the stroma 62 may have a base LIOB threshold of 1, Bowman's membrane 60 may have a relative LIOB threshold of 2 and the epithelium 58 may have a threshold of 0.5. Between the layers of corneal tissue are the interfaces 40 that are of general importance for the present invention. Specifically, the removal or destruction of the portion of one tissue adjacent an interface 40 can be achieved without damage to the other layer of tissue adjacent the interface 40. In addition, due to the natural delineation between layers of tissue at the interface 40, very precise photoablation can be achieved.

Figure 4:
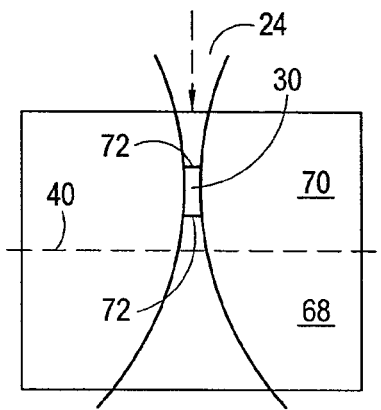
FIG. 4 is a schematic view, not to scale, of a section of the cornea seen in FIG. 3, showing the shape of the laser beam used to ablate a portion of the targeted material with the targeted material positioned downstream of the interface.
Figure 5:
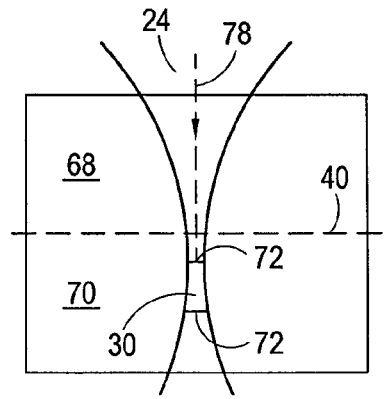
FIG. 5 is a schematic view of a section through the cornea, as in FIG. 4, showing the shape of the laser beam used to ablate a portion of the targeted material with the targeted material positioned upstream of the interface.

Referring now to FIGS. 4 and 5, a laser beam 24 is shown being generally directed to an interface 40 between a targeted material 68 and a non-targeted material 70. Specifically, the laser beam 24 is focused such that its focal point 30 is positioned in the non-targeted material 70. The maximum beam energy density reached at the focal point 30 is insufficient to photoablate the non-targeted material 70 due to the proper selection of beam parameters such as intensity, geometry and pulse duration. Equidistantly spaced from the focal point 30 are beam positions 72 at which a minimum beam energy density is reached. As indicated by the arrow indicating the path of the laser beam 24 in FIG. 4, the non-targeted material 70 is positioned upstream of the interface 40. Therefore, the laser beam 24 does not pass through the targeted material 68 before reaching its focal point 30. Conversely, in FIG. 5, the targeted material 68 is positioned upstream of the interface 40 such that the laser beam 24 passes therethrough before reaching its focal point 30. Both of FIGS. 4 and 5 depict a preferred starting point for the photoablation procedure in which the focal point 30 is positioned in the non-targeted material 70 such that photoablation does not occur in the targeted material 68.

Figure 6:
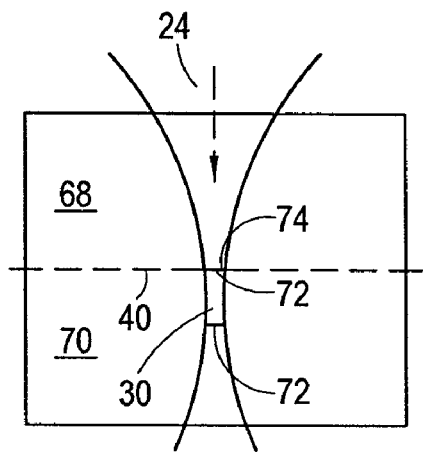
FIG. 6 is a schematic view of the cornea, as in FIG. 5, with the focal point of the laser beam moved to the interface.
Figure 7:
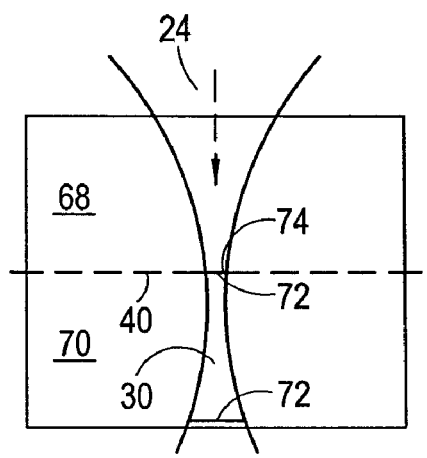
FIG. 7 is a schematic view of the cornea, as in FIG. 5, with the energy level of the laser beam increased to move the position of the minimum beam energy density to the interface.

Referring now to FIG. 6, the laser beam 24 of FIG. 5 is shown after advancement of the focal point 30 (and the position 72 of minimum beam energy density) toward the interface 40. Specifically, FIG. 6 shows that the minimum beam energy density contacts the targeted material 68 and causes a portion 74 of the targeted material 68 to be photoablated. Similarly, FIG. 7 shows the laser beam 24 of FIG. 5 after advancement of the position 72 of minimum beam energy density due to an increase in intensity of the beam 24. Again, the minimum beam energy density contacts the targeted material 68 and causes a portion 74 of the targeted material 68 to be photoablated.

Figure 9:
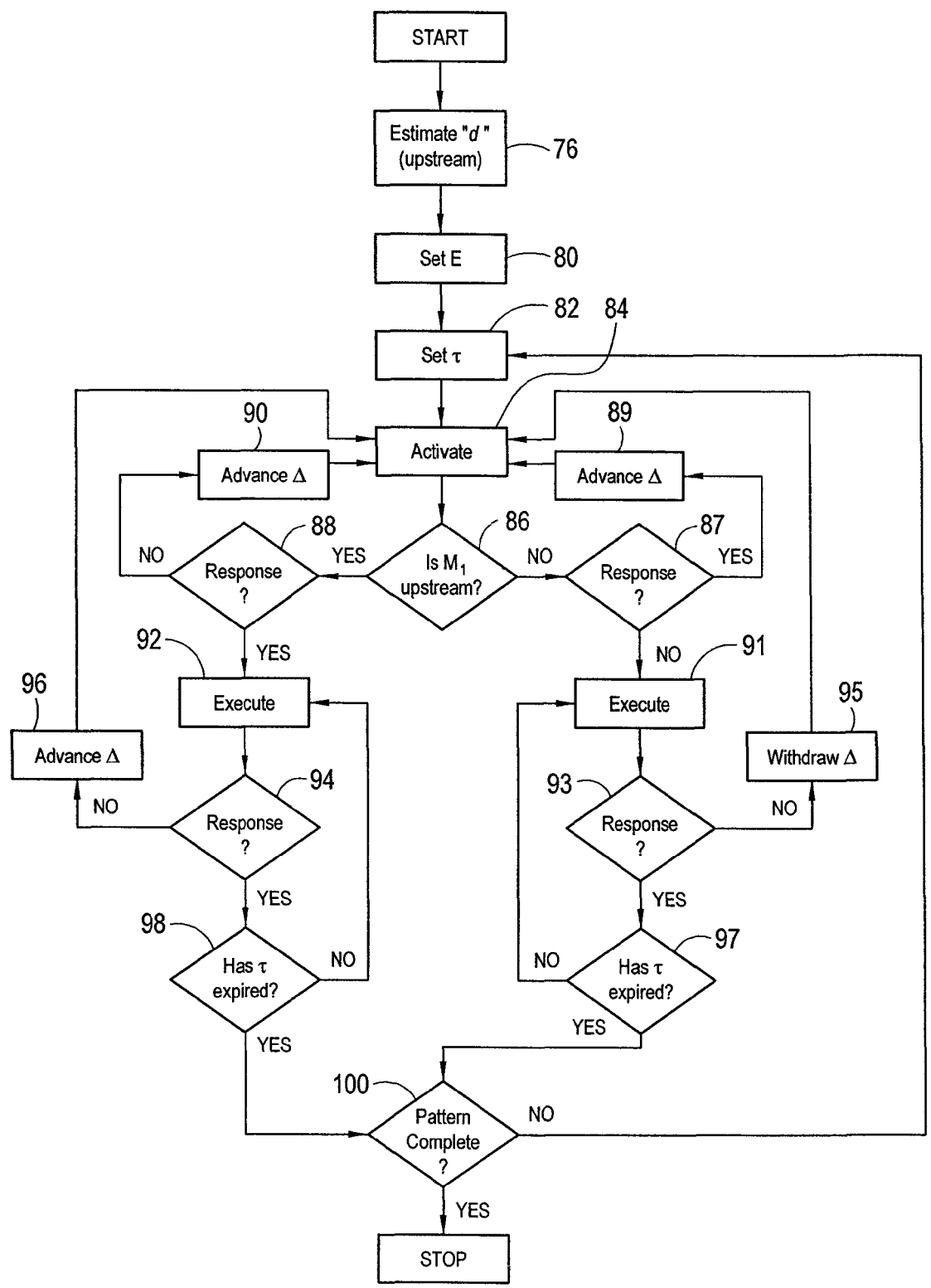
FIG. 9 is a logic flow chart of the sequential steps to be accomplished in accordance with the methods of the present invention.

Referring now to FIG. 9, it will be seen that in the operation of laser system 20, the performance of the methods of the present invention begins by estimating the depth "d" at which the focal point 30 will be positioned in the eye 22 (action block 76). Specifically, the interface 40 between the targeted material 68 and non-targeted material 70 is found. Then the depth necessary to place the focal point 30 in the non-targeted material 70 near the interface 40 is estimated. In FIG. 6, the estimated distance 78 is shown establishing the focal point 30 in the non-targeted material 70. In order to provide the appropriate beam energy densities in the non-targeted material 70 and targeted material 68, the beam parameters such as the intensity or energy level "E" and the treatment duration "τ" are set (action blocks 80 and 82). It is assumed that the ablation energy thresholds of the targeted material 68 and non-targeted material 70 are known before these steps are taken. Of course, the thresholds may be estimated if they are not previously identified.

Once the desired parameters are set, the system 20 is activated to generate the pulsed laser beam 24 (action block 84). Based on the answer to inquiry block 86, i.e. whether the non-targeted material 70 (i.e., "$M_1$") is upstream from the interface 40, specific steps are taken depending on whether the sensor 42 identifies any photoablated targeted material 68 in response to the laser beam 24. As is known, photoablation of material such as corneal or biological tissue causes formation of a bubble or plasma that can be sensed by the sensor 42.

Assuming that the non-targeted material 70 is upstream from the interface 40, then inquiry block 88 is reached. If no targeted material 68 is photoablated, then the position 72 of the minimum beam energy density is advanced (action block 90). As shown in FIGS. 6 and 7, such advance may be performed by moving the focal point 30 toward the interface 40 or by increasing the energy level of the laser beam 24. After the advance of the position 72 of the minimum beam energy density, the system 20 is again activated at action block 84 to generate the pulsed laser beam 24. In this way, the position 72 of the minimum beam energy density is advanced toward the targeted material 68 until photoablation occurs.

When photoablation occurs and there is a positive response to inquiry block 88, then the laser system 20 is executed to scan the laser beam 24 to a new location in the non-targeted material 70 (action block 92). Here, a loop such as that discussed above is again encountered to ensure that the position 72 of the minimum beam energy density be advanced toward the targeted material 68 until photoablation occurs at the new location. Specifically, inquiry block 94 requires, if photoablation does not occur, that the position 72 of the minimum beam energy density be advanced toward the targeted material 68 (action block 96) before the beam 24 is again activated (action block 84). If photoablation does occur, then it is determined whether the treatment duration has expired (inquiry block 98). If It has not expired, the method is restarted at the scanning step of action block 92. If it has expired, then it is determined whether the photoablation pattern of the targeted material 68 is complete (inquiry block 100). If the entire pattern is completed, then the procedure is completed and the actions are stopped. If not, the procedure is begun again at action block 82.

Turning back to inquiry block 86, the situation where the non-targeted material 70 is not upstream from the interface 40 must be addressed. In this case, inquiry block 87 asks whether any targeted material 68 is photoablated in response to the activation of the laser beam 24. If targeted material 68 is photoablated, then the position 72 of the minimum beam energy density is advanced (action block 89). Such an advance may be performed by moving the focal point 30 toward or into the non-targeted material 70 or by decreasing the energy level of the laser beam 24. After advancing the position 72 of the minimum beam energy density, the laser beam 24 is again activated at action block 84 to generate the pulsed laser beam 24. In this way, the position 72 of the minimum beam energy density is advanced toward the non-targeted material 70 until photoablation does not occur in response to the activation of the laser beam 24. This loop ensures that photoablation will occur only in the portion 74 of the targeted material 68 that is adjacent the interface 40.

Once photoablation does not occur in response to the activation of the laser beam 24, it is known that the focal point 30 is properly positioned in the non-targeted material 70. The beam 24 can then be scanned to a new location in the non-targeted material 70 (action block 91). Here, a loop such as that discussed above is again encountered to ensure that the position 72 of the minimum beam energy density be withdrawn toward the targeted material 68 until photoablation occurs at the new location. Specifically, inquiry block 93 requires, if photoablation does not occur, that the position 72 of the minimum beam energy density be withdrawn toward the targeted material 68 (action block 95) before the beam 24 is again activated (action block 84). If photoablation does occur, then it is determined whether the treatment duration has expired (inquiry block 97). If it has not expired, the method is restarted at the scanning step of action block 91. If it has expired, then it is determined whether the photoablation pattern of the targeted material 68 is complete (inquiry block 100). If the entire pattern is completed, then the procedure is completed and the actions are stopped. If not, the procedure is begun again at action block 82.

Figure 10:
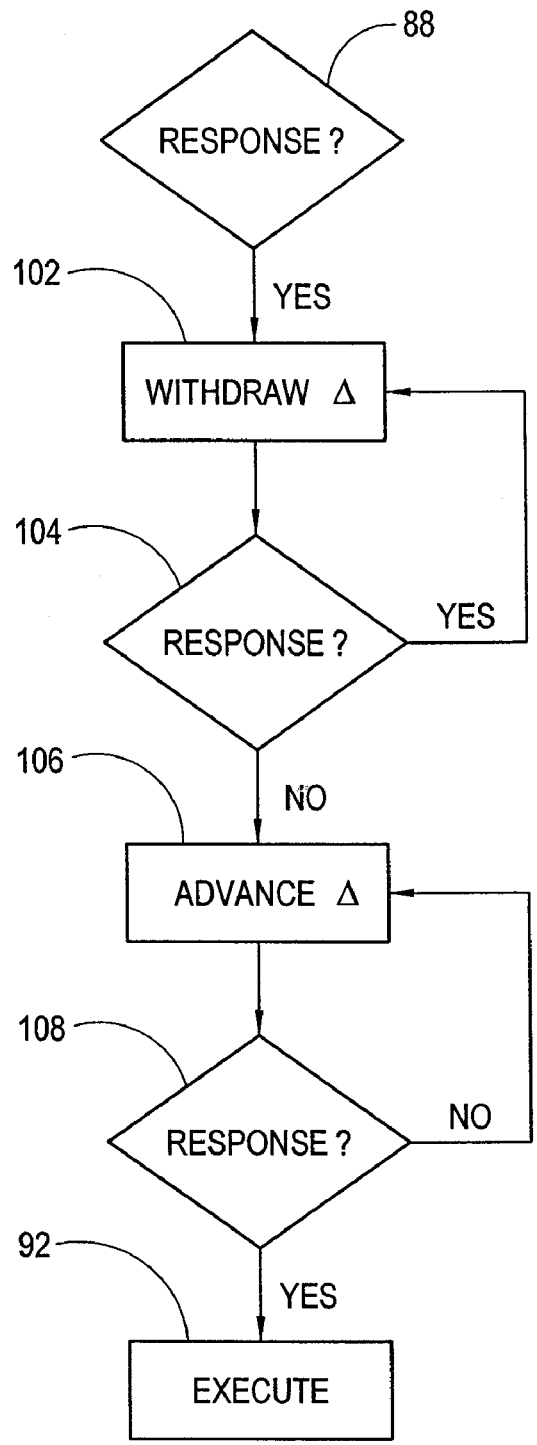
FIG. 10 is a logic flow chart of additional steps that may be accomplished in accordance with the methods of the present invention.

As shown in FIG. 10, additional steps may be included when the non-targeted material 70 is upstream of the interface 40. Specifically, the method may include a loop to ensure that the focal point 30 is not positioned too deep within the cornea 46 such that the targeted material 68 is photoablated at a location deeper than the interface 40. For instance, if photoablation occurs as a result of the activation of the laser beam 24, then the position 72 of the minimum beam energy density is withdrawn toward the interface 40 (action block 102). If, after such withdrawal, photoablation still occurs (as noted at inquiry block 104), then the position 72 is withdrawn again. Once photoablation does not occur, the minimum beam energy density is known to be at the interface or slightly within the non-targeted material 70. Therefore, the position 72 of the minimum beam energy density is advanced toward the targeted material 68 (action block 106). If photoablation does not occur in response to this advance (as noted at inquiry block 108), the position 72 is advanced again. Upon sensing that photoablation occurs, execution of the scanning process begins at action block 92 and the method returns to the process set forth in FIG. 9.

Figure 8:
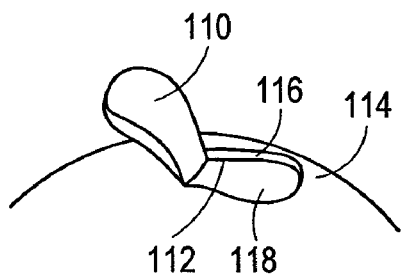
FIG. 8 is a perspective view of a corneal flap created in part using the method of the present invention.

Referring now to FIG. 8, a corneal flap 110 prepared in accordance with the present invention is shown. The flap 110 is prepared by first photoablating a periphery 112 for the flap 110. Because the periphery 112 is formed along the interface 40 between two corneal tissues as discussed above, it is much more precise than a periphery cut through a tissue. With the periphery 112 established, an incision can be made extending from the anterior surface 114 of the cornea 46 to the periphery 112 to establish an edge 116 for the flap 110. Once the edge 116 is created, the flap 110 can be peeled from the remainder of the cornea 46 to expose the surface of the underlying tissue 118. After exposure, the underlying tissue 118 can be photoablated using an excimer laser (not shown). After photoablation with the excimer laser, the flap 110 can be repositioned over the underlying tissue 118 and allowed to heal. The result is a reshaped cornea 46.

While the particular method and device for performing subsurface photoablation as herein shown and disclosed in detail is fully capable of obtaining the objects and providing the advantages hereinbefore stated, it is to be understood that it is merely illustrative of the presently preferred embodiments of the invention and that no limitations are intended to the details of the construction or design herein shown other than as described in the appended claims.

What is claimed is:

1. A method for performing photoablation along an interface between a first material and a second material, with the first material having a higher energy ablation threshold and the second material having a lower energy ablation threshold, the method comprising the steps of:
    selecting a beam geometry, a beam energy, and a pulse duration to create a pulsed laser beam having a beam energy density, with the beam energy density being less than the higher energy ablation threshold and greater than or equal to the lower energy ablation threshold;
    focusing the laser beam to a focal point;
    locating the focal point in the first material near the interface where no photoablation response is obtained; and
    advancing the focal point toward the second material until a photoablation response is obtained in the second material adjacent the interface.

2. A method as recited in claim 1 further comprising the steps of:
    scanning the laser beam along the interface; and
    sequentially repeating said locating step and said advancing step to photoablate another portion of the second material adjacent the interface.

3. A method as recited in claim 2 wherein the first material and the second material are part of the cornea and wherein the scanning and repeating steps are performed until a periphery for a flap is formed, the method further comprising the steps of:
    incising the cornea between the anterior surface of the cornea and the periphery to form an edge, with the flap being bounded by the edge; and
    separating the first material and the second material along the periphery.

4. A method as recited in claim 3 wherein said separating step is performed by mechanically peeling the first material and the second material from one another at the periphery.

5. A method as recited in claim 2 further comprising the steps of:
    withdrawing the focal point toward the first material until no photoablation response is obtained; and
    selectively repeating said advancing and withdrawing steps until the portion of the second material adjacent the interface and nearest the focal point is photoablated.

6. A method as recited in claim 2 wherein the second material extends from the interface to a boundary, and wherein the locating step is accomplished by:
- situating the focal point in the first material or second material;
- sensing whether any second material is photoablated in response thereto;
- identifying that the focal point is in the first material when said sensing step senses no second material is photoablated;
- resituating the focal point away from the boundary of the second material when said sensing step senses that second material is photoablated; and
- repeating said sensing, identifying and resituating steps until the focal point is identified as being in the first material.

7. A method as recited in claim 2 further comprising the steps of:
- determining whether the photoablated material is adjacent the interface when said detecting step detects that second material is photoablated;
- adjusting the focal point away from the second material to an energy density greater than the lower energy density threshold when said determining step indicates that the photoablated material is not adjacent the interface; and
- repeating said determining and adjusting steps until the photoablated material is determined as being adjacent the interface.

8. A method as recited in claim 2 wherein the locating step to find the interface is accomplished by employing a device selected from a group comprising a confocal microscope and an optical coherence tomography.

9. A method as recited in claim 1 wherein the laser beam passes through the first material before reaching the interface.

10. A method as recited in claim 1 wherein the laser beam passes through the second material before reaching the interface.

11. A method as recited in claim 1 wherein the first material is a corneal tissue and the second material is a corneal tissue.

12. A method as recited in claim 11 wherein the first material is Bowman's membrane and the second material is the epithelium.

13. A method for performing photoablation along an interface between a first material and a second material, the method comprising the steps of:
- identifying a higher energy ablation threshold of the first material and a lower energy ablation threshold of the second material;
- generating a pulsed laser beam having a beam energy density that is less than the higher energy ablation threshold and greater than or equal to the lower energy ablation threshold;
- focusing the laser beam to a focal point;
- locating the focal point in the first material near the interface where no photoablation response is obtained; and
- advancing the focal point toward the second material until a photoablation response is obtained in the second material adjacent the interface,
- repeating said locating and advancing steps to photoablate further portions of the second material adjacent the interface.

14. A method as recited in claim 13 wherein the pulsed laser beam has the beam density at a focal point and has a minimum ablation beam density equal to the lower energy ablation threshold, and wherein said directing step is accomplished by:
- placing the minimum ablation beam density in the first material; and
- advancing the minimum ablation beam density toward the interface until the minimum ablation beam density reaches and photoablates the second material.

15. A method as recited in claim 14 wherein the advancing step is accomplished by:
- moving the focal point toward the interface; and/or
- increasing the beam energy density.

* * * * *